United States Patent [19]

Shanbrom

[11] 4,314,997

[45] Feb. 9, 1982

[54] PURIFICATION OF PLASMA PROTEIN PRODUCTS

[76] Inventor: Edward Shanbrom, 2252 Liane La., Santa Ana, Calif. 92705

[21] Appl. No.: 194,264

[22] Filed: Oct. 6, 1980

[51] Int. Cl.$^3$ .................... A61K 35/14; A61K 37/00
[52] U.S. Cl. .................................. 424/101; 424/177
[58] Field of Search ............... 424/78, 199, 243, 303, 424/311, 315, 316, 319, 325, 329, 335, 339, 340, 101, 177

[56] References Cited
PUBLICATIONS

Klose et al., Chem. Abst., vol. 92 (1980) p. 194,006z.
Asculai et al., Chem. Abst., vol. 89 (1978) p. 54,107s.
Funakoshi, Chem. Abst., vol. 84 (1976) p. 111,640n.

*Primary Examiner*—Sam Rosen
*Attorney, Agent, or Firm*—Eric P. Schellin

[57] ABSTRACT

Plasma, plasma derivatives and products thereof are subjected to prolonged contact with a solution or suspension of from about 0.25% to about 10% by weight of a non-denaturing amphiphile to cause irreversible destruction of endotoxins, destruction of thromboplastic-like coagulation activating substances and inactivation of hepatitis viruses (B and non-A, non-B).

10 Claims, No Drawings

PURIFICATION OF PLASMA PROTEIN PRODUCTS

BACKGROUND OF THE INVENTION

This invention relates to a method of reducing the pyrogenicity, hepatitis infectivity and clotting activation of plasma, plasma derivatives and products thereof.

In the development of new products from human plasma, at least three major problems are always present. These are contamination with pyrogens (endotoxins), transmission of viral hepatitis, and activation of the coagulation enzymes.

Pyrogens are lipopolysaccharides (LPS) derived from the outer cell wall of gram-negative bacteria. They are toxic materials which are also known as endotoxins to distinguish them from toxic substances synthesized and excreted by the intact bacterium. Pyrogens have numerous biologic activities which include the production of fever, activation of clotting mechanisms and induction of shock. Consequently, it is essential that pyrogenic substances be removed and that the causative bacteria be rendered innocous by sterilization or other such treatment of the final plasma product.

Prior methods for such inactivation or destruction of pyrogens comprise extensive treatment with heat, acid or alkali, filtration of insoluble pyrogens, or removal by adsorption with gels, ion-exchange resins and various other such adsorbent materials. Most of these methods are burdensome, time consuming, or destructive of the protein due to the rigorousness of the treatment.

Further background on the properties and effects of pyrogens can be had by reference to a paper by Elizabeth Work entitled "Production, Chemistry and Properties of Bacterial Pyrogens and Endotoxins" in "Pyrogens and Fever", Ciba Foundation Symposium, 1971, pp. 23-47, edited by Wolstenholme and Birch, published by Churchill Livingstone; and a paper by D. C. Morrison and R. J. Ulevitch entitled "The Effects of Bacterial Endotoxins on Host Mediation Systems" in *Amer. J. Pathol.* 93 (2), 527-601 (1978).

It is well-known that plasma and products made from plasma may transmit hepatitis. Until recently, interest has focused primarily on hepatitis B antigen ($HB_sAg$) as the offending agent and attempts at eliminating this agent have led to widespread screening of all plasma used in transfusing by a variety of laboratory procedures. While such laboratory screening has apparently decreased the incidence of hepatitis B in patients receiving whole blood transfusions, there has not been significant improvement in the incidence of the disease transmitted from plasma products. Attempts to remove the virus by various adsorption procedures or precipitation techniques, e.g. with polyethylene glycol, have not proven to eliminate infectivity. There is some evidence that the combination of ultraviolet light and $\beta$-propionolactone may be helpful in inactivating the virus in certain plasma products. However, there is some apprehension that $\beta$-propionolactone has carcinogenic properties.

While the development of screening tests for hepatitis B has been of limited value in reducing transmission of the disease, the identification of this virus (as well as the hepatitis A virus) has led to the recognition of a third virus which is apparently responsible for the majority of cases of hepatitis transmitted by blood plasma derivatives. This virus is referred to as "non-A, non-B hepatitis". Tests for this virus are not yet commercially available for widespread screening. This virus closely resembles hepatitis B virus but is antigenically distinguishable. Both hepatitis B virus and non-A, non-B hepatitis virus appear to have similar structural characteristics and exist as particles containing a DNA core and a lipoprotein membrane.

Attempts to prevent activation of clotting enzymes have centered around the addition of classic anticoagulating chemicals such as citrate, EDTA and heparin. While such measures are partially effective, none of these anticoagulants are effective at the early stage of the clotting sequence which is triggered by activation of Factor XII. Activation of clotting factors may still occur because coagulation may be instigated by the presence of phospholipids from blood platelets. Virtually all blood fractions collected today contain thromboplastic-like substances or phospholipids from platelets and platelet derivatives which activate coagulation. Administration of therapeutic blood fractions which contain these phospholipid particles may be potentially dangerous because of their ability to induce unwanted intravascular coagulation.

DESCRIPTION OF THE INVENTION

In accordance with the present invention, plasma, plasma derivatives and products thereof are subjected to prolonged contact with a solution or suspension of from about 0.25% to about 10% by weight of a non-denaturing amphiphile. For convenience, these treated substances are hereinafter referred to as "plasma protein products". The term "non-denaturing" means non-protein-denaturing. The subject treatment of the plasma protein products causes irreversible destruction of endotoxins, destroys thromboplastic-like coagulation activating substances and substantially reduces the infectivity of hepatitis viruses (B and non-A, non-B). These effects are produced without substantially altering the activity of the plasma proteins.

As used herein, the term "amphiphile" is meant to define a substance containing both hydrophilic water-soluble and hydrophobic water-insoluble groups. Amphiphiles are generally classified into various groups and frequently into the anionic, cationic, ampholytic and non-ionic surfactants. The following are well-known commercially available amphiphiles:

Anionic

Sulphated oxyethylated alkylphenol (Triton W-30);
Sulphated lauryl ether alcohol;
Sodium dodecylbenzenesulfonate (Nacconol NR);
Sodium 2-sulfoethyl oleate (Igepon A);
Sodium N-methyl-N-oleylethanol sulfonate (Igepon T);
Sodium dodecylsulfate;
Sodium cholate;
Sodium deoxycholate;
Sodium dodecylsulfonate;
Sodium dodecyl-N-sarcosinate.

Cationic

Dodecyldimethylbenzylammonium chloride (Triton K-60);
Oxyethylated amines (Ethomeen);
Cetyltrimethylammonium bromide;
Tetradecylammonium bromide;
Dodecylpyrimidinium chloride;
Hexadecyltrimethylammonium chloride.

Ampholytic

Dodecyl β-alanine;
N-dodecylaminoethanesulfonic acid;
Palmitoyllysolecithin;
Dodecyl-N-betaine.

Nonionic

Ethylene oxide-propylene oxide condensates (Pluronic block copolymers) such as described in U.S. Pat. No. 2,674,619;
Oxyethylated alkylphenol (Triton X-100);
Partial esters of $C_{12-22}$ fatty acids (e.g. lauric, palmitic, stearic and oleic acids) and hexitol anhydrides (e.g. hexitans and hexides) (Spans) such as described in U.S. Pat. Nos. 2,232,820; 2,232,821; 2,303,432;
Polyoxyethylated derivatives of said partial esters made by adding polyoxyethylene chains to the nonesterified hydroxyls (Tweens, e.g. Tween 80 or Polysorbate 80) such as described in U.S. Pat. No. 2,380,166;
Poloxyethylene partial fatty acid esters (Myrj 45);
Polyoxyethylene fatty alcohol ethers (Brij).

The nonionic surfactants are preferred amphiphiles for use in this invention. The most preferred amphiphiles are the nonionic surfactants having a high water solubility and selected from the group consisting of substances having the general formula $RC_6H_4(OC_2H_4)_nOH$ wherein R is octyl or nonyl and n is at least 3. A most preferred substance of the foregoing general formula is octyl phenoxy polyethoxy ethanol. Surfactants of the latter type are available commercially from Rohm & Haas Co. under the trademark "Triton X", e.g., Triton X-100, Triton X-165, Triton X-205, Triton X-305 and Triton X-405. Another such nonionic surfactant is nonyl phenoxy polyethoxy ethanol which is available commercially under the trademark "Triton N-100".

Another preferred group of amphiphiles are the salts of bile acids such as sodium cholate and sodium deoxycholate.

Treatment of the plasma protein product with the amphiphile can be carried out at any stage in the production process for destroying endotoxin or infectivity of hepatitis virus and preventing of clotting activation. The amphiphile can be added to the starting material or it can be added at some later step in the production sequence.

In the case of therapeutic plasma protein products it will generally be desirable to remove the amphiphile following the prolonged contact with the plasma protein product. In the case of non-therapeutic plasma protein products it will generally be unnecessary to remove the amphiphile. For example, blood plasma and blood fractions for administration to human patients would be subjected to a step for ultimate removal of the amphiphile following the prolonged contact whereas clinical sera for diagnostic purposes generally would not require such removal. Removal of the amphiphile can be carried out by various precipitation steps in which the plasma proteins are precipitated while the amphiphile remains dissolved or suspended in the supernatant. Conventional plasma protein precipitants can be used for this purpose such as, e.g., polyethylene glycol, Pluronic polymers, glycine, ammonium sulfate, alcohol and rivanol.

The period of time during which the plasma protein product is contacted with the amphiphile should be sufficient to cause irreversible destruction of endotoxins and/or inactivation of hepatitis viruses. Generally, a period of from about 30 minutes to about 4 hours at a temperature of from about one degree C. to about 50° C. is adequate to provide the desired destruction of endotoxins and inactivation of hepatitis viruses. It will be appreciated, however, that for non-therapeutic and non-human administration of plasma protein products, the destruction of endotoxins is not critical although the destruction of hepatitis infectivity is important to avoid spread of the virus to the laboratory workers.

The actual contact of the plasma protein products with the amphiphile can be carried out by washing the product with a solution or suspension of the amphiphile or by immersing or soaking the product in such solution or suspension or by admixing the product with such solution or suspension under the aforesaid time and temperature conditions.

Although certain amphiphiles such as sodium deoxycholate have been reported heretofore as able to dissociate or disaggregate endotoxins, the disaggregation has been described as reversible in the presence of the amphiphile tested. These amphiphiles thus have not been previously suggested as able to produce irreversible disaggregation of endotoxins such as to make them practical for the treatment of plasma protein products which are to be used for human administration. See, e.g., the paper by Elizabeth Work, cited hereinbefore. In accordance with the present invention, the desired plasma protein product is precipitated with protein precipitants, as described above, after treatment with the amphiphile to destroy the endotoxins followed by separation and removal of the amphiphile in the supernatant. In such case it has been found that the Lipid A or most active portion of the endotoxin which normally is insoluble in water, remains with the amphiphile in the supernatant. The disaggregation is irreversible and treatment previously not believed to be useful is now rendered practical.

Similarly, although certain other amphiphiles such as Triton X-100, Tween 80, Nonidet NP-40, and sodium dodecylsulfate have been reported heretofore as able to dissociate or disaggregate the hepatitis virus antigen, the disaggregation has been described for the purpose of merely dispersing the antigen or for purifying the antigen for its use in preparing vaccines. See, e.g., U.S. Pat. Nos. 4,118,748; 4,118,749; 4,164,565; and a paper by Johnson et al., *J. Lab. Clin. Med.* 88 (1), 91–101 (1976). As distinguished from the above, treatment of the plasma protein product with the amphiphile under the conditions herein described according to the present invention is to substantially reduce the infectivity of hepatitis viruses in such products whereby the plasma protein product is itself improved.

Testing for the presence of pyrogens and/or to ensure adequate destruction of endotoxins in the plasma protein product can be carried out by the standard qualitative fever response test in rabbits for pyrogens or by more recently developed Limulus lysate (amebocytes) assay procedures for pyrogens (LAL tests). The latter tests are based on gelling of a pyrogenic preparation in the presence of the lysate of the amebocytes of the horseshoe crab (*Limulus polyphemus*). See, e.g., U.S. Pat. No. 4,096,091 for a typical LAL test.

Testing for the presence of hepatitis virus and/or to determine its destruction following treatment of the plasma protein product according to the present invention can be carried out by various conventional laboratory test methods such as reversed passive hemagglutination assays, counterelectrophoresis (CEP) and the more recently developed radioimmunoassay (RIA) procedures. Solid phase RIA procedures for hepatitis antigen as described in U.S. Pat. Nos. 3,867,517 and 4,012,494 and commercially available from Abbott Laboratories under the trademark "Ausria" are illustrative of suitable methods. It should be understood, however, that the determination of the presence of hepatitis antigen is limited by the sensitivity of these tests and that negative test results do not rule out the possible presence of the antigen is extremely low, non-detectable levels.

The present invention is applicable to all types of plasma protein products for therapeutic as well as non-therapeutic uses. Examples of such products are:

Blood and blood fractions such as antihemophilic factor A (AHF, Factor VIII); prothrombin complex (Factors II, VII, IX AND X): gamma globulin; albumin; and the like;

Clinical diagnostic control sera containing human or animal (e.g., porcine or bovine) plasma protein components (e.g., albumin); and Placenta plasma proteins.

The following examples will further illustrate the invention although it will be understood that the invention is not limited to these specific examples.

EXAMPLE 1

Whole human blood plasma was diluted 1:2 with pyrogen-free water and then spiked with ten micrograms of *E. coli* endotoxin. Triton X-100 was added to a concentration of 2% and the mixture was then incubated at 37° C. for one hour. Three dilutions of the treated mixture were then made and the dilutions were tested for pyrogenicity by the Limulus lysate (amebocytes) assay (LAL test) with the following results:

| Blood Dilutions | Endotoxin Amount | % Triton X-100 | LAL Reaction |
|---|---|---|---|
| 1:10 | 1 microgram | 0.2 | Negative |
| 1:100 | 0.1 " | 0.02 | " |
| 1:1000 | 0.01 " | 0.002 | " |

EXAMPLE 2

A commercially produced vial (lyophilized) of prothrombin complex (25 units of Factor IX per ml when reconstituted) was reconstituted with ten ml of sterile water. Triton X-100 was added to a concentration of 2% and the mixture was incubated ninety minutes at ambient temperature (ca. 20°–22° C.). To nine ml of the above mixture was added 6.0 ml of a 50% solution of polyethylene glycol 4000. The pH was adjusted to 5.7 and the mixture was cooled to below 5° C. to precipitate the protein. The mixture was centrifuged and the precipitate was resuspended in sterile water. The treated product was tested for pyrogenicity by the LAL test and compared with the original untreated sample and a control which consisted of the aforesaid precipitate of the treated sample to which 40 picograms of endotoxin were added. The following results were observed:

| | LAL Reaction | | | |
|---|---|---|---|---|
| Dilutions | 1:10 | 1:20 | 1:40 | 1:80 |
| Original Sample Untreated Precipitate of Sample with 40 picograms Endotoxin | pos. × 2 | pos. × 2 | pos. × 2 | pos. × 2 |
| Triton X-100 treated Precipitate | neg.* | pos. × 2 | pos. × 2 | pos. × 2 |
| | neg. × 2 | neg. × 2 | neg. × 2 | neg. × 2 |

*Due to heparin inhibitory effect at this dilution
pos. × 2 = positive in duplicate testing
neg. × 2 = negative in duplicate testing

EXAMPLE 3

Similar depyrogenation of endotoxin-contaminated albumin is obtained by treatment with 2% Triton X-100 as in Examples 1 and 2, above, or with 2% Polysorbate 80.

EXAMPLE 4

Similar depyrogenation of endotoxin-contaminated fibrinogen is obtained by treatment with 2% Triton X-100 as in Examples 1 and 2, above, or with 2% Polysorbate 80.

EXAMPLE 5

Clinical diagnostic control sera were analyzed for their various components both before and after treatment with Triton X-100 at a concentration of 2% to destroy endotoxins and substantially reduce hepatitis virus infectivity in accordance with the present invention. The following results on the untreated and treated product show that the Triton X-100 treatment has not substantially altered the activity of the various components in the control sera.

| Analyte | Untreated (Control) | Treated |
|---|---|---|
| Calcium (mg/dl) | 14.3 | 13.4 |
| Phosphorus (mg/dl) | 3.5 | 3.4 |
| Glucose (mg/dl) | 235 | 219 |
| BUN (mg/dl) | 53 | 50 |
| Uric acid (mg/dl) | 8.1 | 7.9 |
| Cholesterol (mg/dl) | 186 | 172 |
| Total protein (gm/dl) | 8.4 | 8.2 |
| Albumin (gm/dl) | 4.7 | 4.4 |
| Tot. bilirubin (mg/dl) | 3.9 | 3.8 |
| Alk. phosphatase (IU/L) | 162 | 145 |
| LDH (IU/L) | 325 | 412 |
| SGOT (IU/L) | 105 | 103 |
| Sodium (meq/l) | 146 | 139 |
| Potassium (meq/l) | 5.7 | 5.3 |
| Chloride (meq/l) | 111 | 107 |
| Carbon dioxide (meq/l) | 28 | 26 |
| Creatinine (mg/dl) | 3.4 | 3.1 |
| SGPT (IU/L) | 118 | 107 |
| Uric Acid (mg/dl) (Hycel Mark X) | 8.8 | 8.1 |
| Uric Acid (mg/dl) (12/60, 6/60) | 8.5 | 8.3 |

The aforesaid analysis was made on Technicon 12/60, 6/60 AutoAnalyzer equipment except as noted for uric acid on a Hycel Mark X.

EXAMPLE 6

Various therapeutic blood plasma protein products are treated by prolonged contact with a solution of 2%

Triton X-100 and subsequently separated from the Triton X-100 by precipitation as follows:

(a) For the production of AHF, Triton X-100 is added to whole blood plasma prior to the conventional cryoprecipitation step at freezing temperatures of −20° C. to −80° C. The Triton X-100 remains in the supernatant while AHF is concentrated in the cryoprecipitate.

(b) For the production of gamma globulin, Triton X-100 is added to whole blood plasma at the beginning of the Cohn fractionation procedure with cold alcohol according to Method 6. The Triton X-100 remains in the supernatant while gamma globulin is precipitated in Cohn fraction II+III.

(c) For the production of albumin, Triton X-100 is added to the supernatant after the removal of Cohn fraction II+III in the Cohn fractionation procedure with cold alcohol according to Method 6. The Triton X-100 remains in the supernatant while albumin is precipitated principally in Cohn fraction V.

(d) For the reworking of pyrogenic albumin, albumin powder is resuspended and Triton X-100 is added to the suspension. Albumin is then reprecipitated with a protein precipitant such as polyethylene glycol, alcohol or ammonium sulfate and Triton X-100 remains in the supernatant.

EXAMPLE 7

Various non-therapeutic blood plasma protein products such as fetal bovine serum, bovine albumin and bovine serum which are commonly used as growth media in tissue culture procedures are treated by prolonged contact with 2% Triton X-100 as in the previous examples. The Triton X-100 is removed in the supernatant after precipitation of all proteins as in Example 6 and resuspension in appropriate milieu, e.g., balanced salt solution, such as Hank's BSS.

EXAMPLE 8

When 2% Triton X-100 is added to platelet-poor plasma (double spun plasma) the non-activated partial thromboplastin time (PTT) becomes indefinitely prolonged instead of the usual 200 seconds. This evidences the anticoagulant activity of Triton X-100 in the plasma.

(a) Whole blood collected in 2% Triton X-100 does not clot for over 12 hours.

(b) Whole blood collected in 2% sodium cholate does not clot in over 24 hours.

EXAMPLE 9

Samples of blood sera and plasma obtained for laboratory analysis are placed in test tubes containing 2% Triton X-100 and allowed to incubate for 30–120 minutes to inactivate potential hepatitis virus.

Various other examples will be apparent to the person skilled in the art after reading the present disclosure without departing from the spirit and scope of the invention and it is intended that all such examples be included within the scope of the appended claims.

What is claimed is:

1. The method of reducing pyrogenicity, hepatitis infectivity and clotting activation of a plasma protein product comprising treatment of said product by prolonged contact with a solution or suspension of from about 0.25% to about 10% by weight of a non-denaturing amphiphile, followed by addition to the treatment mixture of a plasma protein precipitant to precipitate said plasma protein product and then separating said precipitate from the supernatant.

2. The method of claim 1 in which the amphiphile is a bile acid salt selected from the group consisting of sodium cholate and sodium deoxycholate.

3. The method of claim 1 in which the amphiphile is a nonionic surfactant.

4. The method of claim 3 in which the nonionic surfactant is selected from the group consisting of the polyoxyethylated derivatives of partial esters of $C_{12-22}$ fatty acids and hexitol anhydrides.

5. The method of claim 4 in which the nonionic surfactant is Polysorbate 80.

6. The method of claim 3 in which the nonionic surfactant is selected from the group consisting of substances having the general formula $RC_6H_4(OC_2H_4)_nOH$ wherein R is octyl or nonyl and n is at least 3.

7. The method of claim 6 in which the nonionic surfactant is octyl phenoxy polyethoxy ethanol.

8. The method of claim 7 in which the concentration of the surfactant is about 2%.

9. The method of claim 1 in which the plasma protein product is a therapeutic blood plasma fraction and in which the amphiphile is removed from said product following said prolonged contact by precipitation of said plasma fraction with a plasma protein precipitant comprising polyethylene glycol while said amphiphile remains dissolved or suspended in the supernatant.

10. The method of claim 9 in which the amphiphile is octyl phenoxy polyethoxy ethanol.

* * * * *